(12) United States Patent
Baust

(10) Patent No.: US 9,877,767 B2
(45) Date of Patent: Jan. 30, 2018

(54) ENDOSCOPIC CRYOABLATION CATHETER

(71) Applicant: CPSI Holdings LLC

(72) Inventor: John M Baust, Owego, NY (US)

(73) Assignee: CPSI Holdings LLC, Owego, NY (US)

( * ) Notice: Subject to any disclaimer, the term of this patent is extended or adjusted under 35 U.S.C. 154(b) by 191 days.

(21) Appl. No.: 13/937,658

(22) Filed: Jul. 9, 2013

(65) Prior Publication Data

US 2014/0275767 A1    Sep. 18, 2014

Related U.S. Application Data

(60) Provisional application No. 61/783,488, filed on Mar. 14, 2013.

(51) Int. Cl.

| A61B 18/02 | (2006.01) |
| A61B 10/02 | (2006.01) |
| A61B 17/32 | (2006.01) |
| A61B 18/08 | (2006.01) |
| A61B 18/14 | (2006.01) |
| A61B 18/22 | (2006.01) |
| A61B 18/00 | (2006.01) |
| A61B 10/04 | (2006.01) |

(52) U.S. Cl.
CPC .......... *A61B 18/02* (2013.01); *A61B 10/0233* (2013.01); *A61B 10/0283* (2013.01); *A61B 10/04* (2013.01); *A61B 17/320068* (2013.01); *A61B 18/082* (2013.01); *A61B 18/1477* (2013.01); *A61B 18/22* (2013.01); *A61B 2018/00005* (2013.01); *A61B 2018/00482* (2013.01); *A61B 2018/00577* (2013.01); *A61B 2018/00595* (2013.01); *A61B 2018/0212* (2013.01); *A61B 2018/0293* (2013.01); *A61B 2018/1425* (2013.01); *A61B 2218/007* (2013.01)

(58) Field of Classification Search
CPC .. A61B 2018/0041; A61B 2018/00196; A61B 2018/00916; A61B 2018/00922; A61B 2018/00976; A61B 2018/0293
See application file for complete search history.

(56) References Cited

U.S. PATENT DOCUMENTS

| 3,270,744 A | * | 9/1966 | Katz et al. ...................... 606/25 |
| 3,859,986 A | * | 1/1975 | Okada ................ A61B 1/00098 |
| | | | 600/104 |
| 4,946,460 A | * | 8/1990 | Merry .................... A61B 18/02 |
| | | | 606/21 |
| 5,078,713 A | * | 1/1992 | Varney ................... A61B 18/02 |
| | | | 606/22 |

(Continued)

*Primary Examiner* — Ronald Hupczey, Jr.
(74) *Attorney, Agent, or Firm* — Hoffman Warnick LLC

(57) ABSTRACT

An endoscopic cryoablation apparatus for the ablation of unwanted tissues is disclosed. A method of utilizing the apparatus for ablating pancreatic cancer, gastrointestinal cancers, or other undesired tissue is also incorporated. The apparatus provides a cryoprobe needle tip covered by an outer sheath at a distal end of a catheter shaft such that the distal end includes a defined ablation zone. As implemented, the cryocatheter can be utilized alone or in combination with and endoscopic ultrasound. A moveable handle attached to the outer sheath is configured such that the handle retracts and protracts the outer sheath to expose and cover, respectively, the cryoprobe needle tip.

29 Claims, 5 Drawing Sheets

(56) References Cited

U.S. PATENT DOCUMENTS

| | | | | |
|---|---|---|---|---|
| 5,254,116 A * | 10/1993 | Baust | ............... | A61B 18/02 606/21 |
| 5,281,213 A * | 1/1994 | Milder | ............... | A61B 18/02 606/15 |
| 6,551,309 B1 * | 4/2003 | LePivert | ............... | A61B 18/02 606/20 |
| 6,786,902 B1 * | 9/2004 | Rabin | ............... | A61B 18/02 128/898 |
| 6,974,455 B2 * | 12/2005 | Garabedian et al. | ............... | 606/41 |
| 8,915,908 B2 * | 12/2014 | Privitera et al. | ............... | 606/21 |

\* cited by examiner

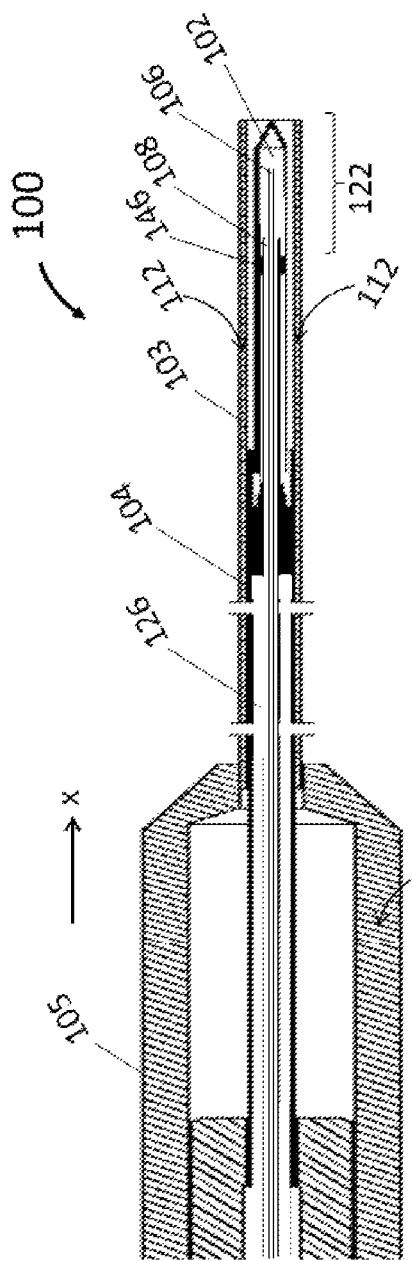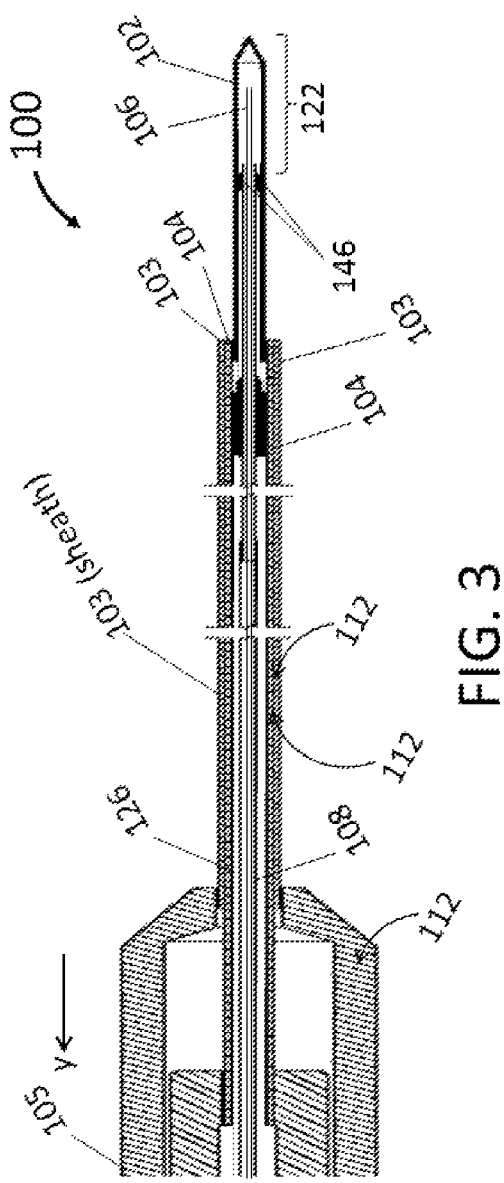

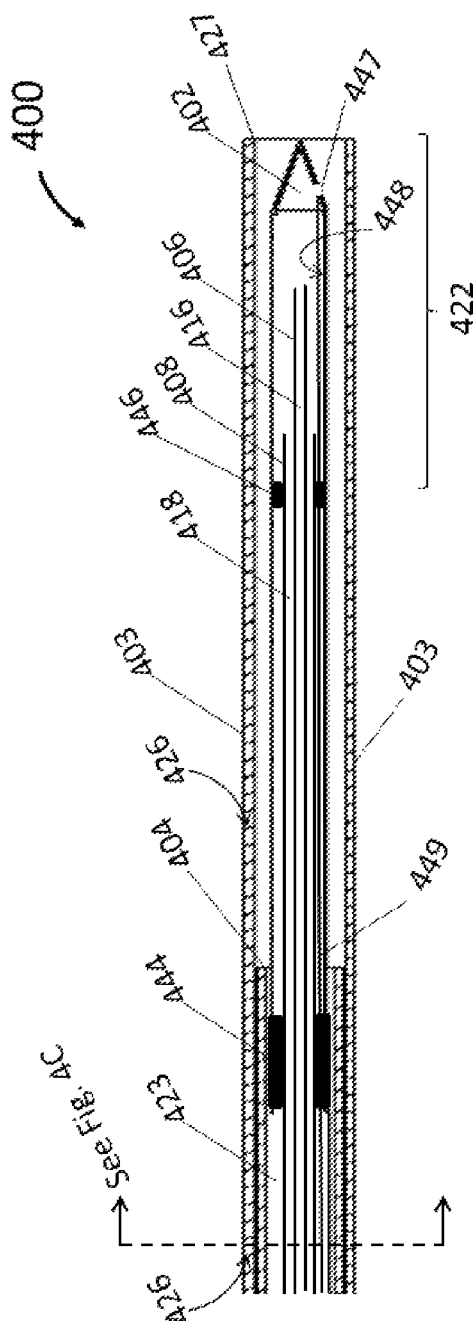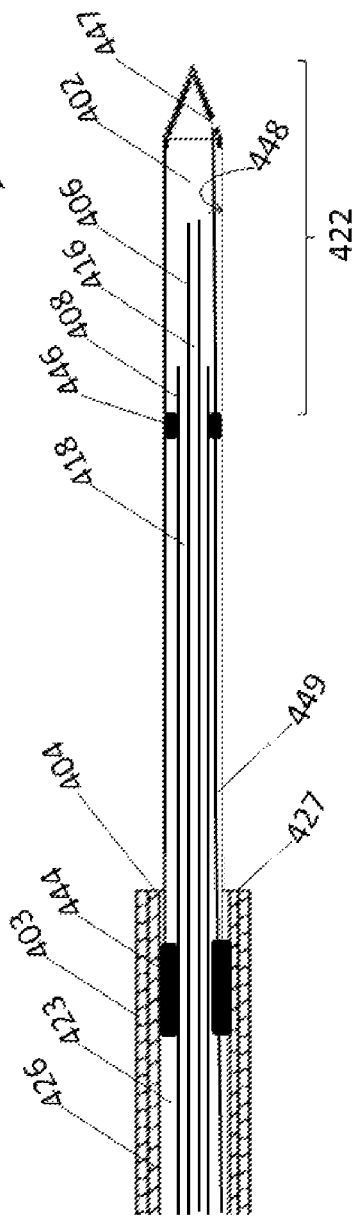
FIG. 4A
FIG. 4B

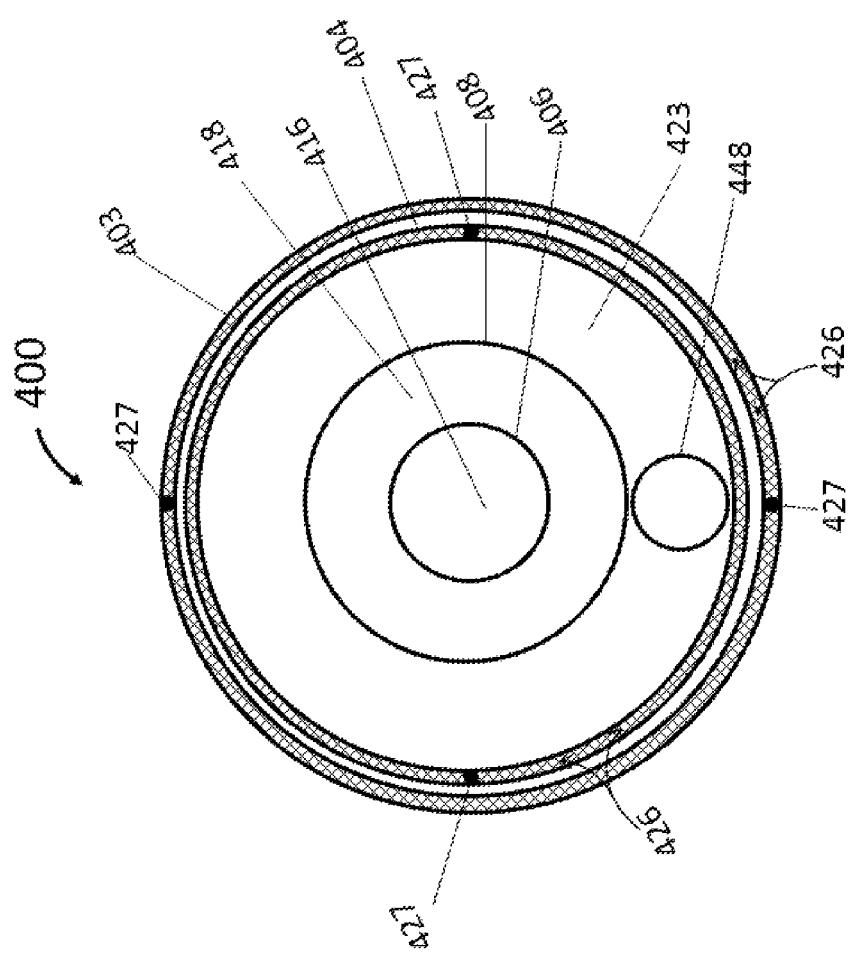

ENDOSCOPIC CRYOABLATION CATHETER

FIELD OF THE INVENTION

The present invention relates generally to medical devices, and, in particular, to a surgical catheter for cryoablation.

BACKGROUND OF THE INVENTION

Pancreatic cancer is one of the major causes of cancer death in Western countries. In 2010, an estimated 43,140 new cases of pancreatic cancer were diagnosed in the United States with an expected five year survival rate of less than about 10%. In about 20% of patients with no metastases, tumor resection is not feasible because of vascular invasion, poor general health, or lacking surgical techniques. The standard treatment for these patients is chemotherapy followed by chemo-radiation therapy, which results in a median survival of eight to twelve months or less.

Current therapeutic options for unresectable pancreatic cancer include radiofrequency ablation (RFA) and cryotherapy. As utilized in the treatment of pancreatic cancer, RFA risks thermal injury to important structures such as the bile duct, the duodenum, and vessels close to the pancreas. A major limitation with RFA is difficulty in assessing the ablated zone by ultrasound, magnetic resonance imaging (MRI) or computed tomography (CT) scan. The poorly perfused pancreatic area also makes it difficult to visualize. Further, studies have demonstrated that radiologic follow-up after ablation could not distinguish inflammatory reactions of the tumor tissue from tumor growth or necrosis within the first four weeks.

Studies have shown the effective use of cryoablation to treat pancreatic cancer via laparoscopic or transcutaneous approach with reduced side effects. Yet, broad based clinical utilization has been limited by commercial devices that do not provide adequate cooling power to effectively treat the cancerous tissue. The invasive nature of surgical (open or laparoscopic) access to the target also remains an ongoing issue along with technological limitations.

In addition, current cryoprobes as used in an endoscopic procedure can cause damage to the endoscope due to freezing of the catheter shaft to the inside of the endoscope. This can interfere with the ultrasound imaging and readjusting or removing the cryoprobe from the tissue or endoscope in a timely manner. Prolonged procedures also can cause freezing of the endoscope to surrounding tissue resulting in damage to non-target tissues such as the esophagus, stomach wall, colon, intestine, rectum or other structure.

For visualization of current pancreatic procedures, endoscopic ultrasound (EUS) has been utilized to image the pancreas in real-time. Issues related to laparoscopic ablation techniques, however, make imaging difficult. For example, anatomical location of the pancreas makes it difficult to visualize and access without damaging other tissues. Development of an effective EUS-guided catheter-based ablation device and treatment method could overcome the problems related to the laparotomy and/or laparoscopic or transcutaneous approaches.

The increasing incidence and high lethality of pancreatic cancer demands the development of new treatment options. An innovative effective endoscopic treatment option for pancreatic cancer would be minimally invasive while enhancing performance and outcome. The improved technology and methodology would reduce levels of disease recurrence, mortality, and damage to non-targeted tissue. Further, the technique would allow for selective ablation of tumor masses. The improved technique would also enhance efficacy of neoadjuvant treatment procedures in patients not suitable for any other kind of treatment. Endoscopic access compatibility would also be highly desired in combination with the use of ablative techniques to reduce procedure time, overall costs, and risks or other complications.

As desired, the improved therapeutic option will offer an effective, minimally invasive therapeutic option for gastroenterologists in the in situ treatment of pancreatic cancer or other gastrointestinal cancers or diseases. Furthermore, patients with any stage of pancreatic disease will benefit from the technology and technique. The treatment option will also reduce the five year mortality rate and reduce the U.S. annual estimated $1.4 billion in pancreatic therapy costs.

An improved endoscopic cryoablation catheter will be compatible with endoscopic instrumentation. Desirably, an EUS-guided cryoablation catheter will be integrally designed with the flexibility and stiffness necessary to place a probe directly though the stomach wall into the pancreatic tumor. The sharp needle-like tip of the probe will be capable of penetrating any desmoplasia, fibrous connective tissue, tumor infiltrate, and scar or fibrosis. Additionally, the sharpness of this needle-like probe can also be used for EUS guided pseudocyst drainage during the procedure. The EUS cryoablation procedure will provide surgeons with a minimally invasive tool that reduces morbidity and lowers costs.

SUMMARY OF THE INVENTION

The present invention utilizes a cryoablation device integrated with an endoscope that facilitates rapid and effective treatment of pancreatic cancer or other gastrointestinal cancers or unwanted tissues. The cryoablation catheter is compatible with any number of cryogens and cryo-devices including but not limited to, argon, carbon dioxide, nitrogen gas, liquid nitrogen, critical and supercritical cryogens, nitrous oxide, dual phase cryogens, and propane, among others. The endoscopic device provides a highly effective, minimally invasive therapeutic option for gastroenterologists to use in the in situ treatment of pancreatic cancer. Further, patients with any stage of pancreatic disease can benefit from the technology.

In one embodiment, a cryoablation device provides a rapid and effective methodology to treat pancreatic cancer endoscopically. Endoscopic access in combination with targeted ablative techniques reduces procedure time, overall costs, and risks associated therewith. The improved endoscopic cryoablation device implements a cryoablation catheter compatible for use within an endoscope. The cryoablation catheter has the flexibility, stiffness, and steerability to place a probe tip located therein directly though the stomach wall and into a pancreatic tumor. The cryoablation catheter is also compatible with any other type of endoscope or colorectal scope for which its introduction and placement can be guided by any other type of visualization technique, including but not limited to external ultrasound, fluoroscopy, CT, MRI, optical and/or video assisted visualization. The sharp needle-like tip of the probe is capable of penetrating any desmoplasia, fibrous connective tissue, tumor infiltrate, and scar or fibrosis, even in patients who have already undergone radiation therapy. Additionally, the sharpness of this needle-like probe is utilized for EUS guided pseudocyst drainage during the procedure.

One embodiment of the endoscopic cryoablation catheter incorporates a cryoablation procedure which provides surgeons with a minimally invasive tool that reduces patient morbidity and lowers costs as compared to laparoscopic or surgical procedures. The method of using the apparatus for endoscopic ablation therapy comprises the steps of: providing an apparatus comprising a cryogen supply line and a cryogen return line surrounded by a catheter shaft, such that the cryogen supply line, the cryogen return line, and the catheter shaft run longitudinally from a proximal end at a cryogen console to a distal end at an ablation zone; wherein the distal end of the catheter shaft is covered by a moveable sheath and the moveable sheath interconnects with a handle; inserting the catheter shaft into an endoscopic path, wherein the sheath covers the ablation zone; positioning the ablation zone to a tissue site; retracting the sheath to expose the ablation zone; delivering cryogenic temperatures to the ablation zone for an allocated treatment time; allowing the ablation zone to thaw or heat; removing the ablation zone from the tissue site; protracting the sheath to cover the ablation zone; and removing the catheter shaft from the endoscopic path.

In particular, the endoscopic cryoablation catheter is designed for use in treating pancreatic cancer in vivo. When positioning the ablation zone, or probe tip, the apparatus is directed through an endoscopic path that enters the stomach. The probe tip is a needle-tip probe that is inserted through a wall of the stomach and directed into the pancreatic tissue. Any number of procedures may be performed at a single treatment site or at various sites within or along an endoscopic path. Where a heating element such as a heating coil is utilized during thaw or active heat ablation, the tissue site can be further damaged. Further, the active heat ablation may be used to cauterize tissue at the treatment site or anywhere along the endoscopic path. As mentioned in detail in the following, any step during the procedure can be motorized, computerized, and/or programmed prior to, during, or following a procedure step in the methodology.

In one embodiment, the endoscopic cryoablation catheter is utilized in combination with other anti-cancer therapies including radiation, RF, chemotherapy, gene therapy, or any other treatment modality in simultaneous or staged delivery.

Furthermore, endoscopic access coupled with targeted in situ cancer destruction reduces procedure time, overall costs, and risks of complication while offering an effective therapeutic option currently unavailable to pancreatic cancer patients

BRIEF DESCRIPTION OF THE DRAWINGS

The accompanying drawings, which are incorporated in and constitute a part of this specification, illustrate various embodiments of the present invention, and, together with the description, serve to explain the principles of the invention. The various features are not necessarily drawn to scale. In fact, the dimensions may be arbitrarily increased or decreased for clarity of discussion. In the drawings:

FIG. 2 is a magnified transparent side view of a distal end of an embodiment of the invention with a covered probe tip.

FIG. 3 is a magnified transparent side view of a distal end of an embodiment of the invention with the cover sheath retracted.

FIG. 4A is magnified view of an embodiment of the invention such that the probe at the distal end is covered by the sheath.

FIG. 4B depicts an embodiment of the invention with the sheath retracted.

FIG. 4C is a cut-away cross section of an embodiment of the invention from FIG. 4A.

DETAILED DESCRIPTION

Reference will now be made in detail to the present embodiments of the invention, examples of which are illustrated in the accompanying drawings. Wherever possible, the same reference numbers will be used throughout the drawings to refer to the same or like parts.

Disclosed herein is the development of an endoscopic cryoablation apparatus for the ablation of undesirable tissue. A method of utilizing the endoscopic cryoablation apparatus to treat pancreatic cancer, gastrointestinal cancer, or other such tissue is also incorporated.

Figure 1:
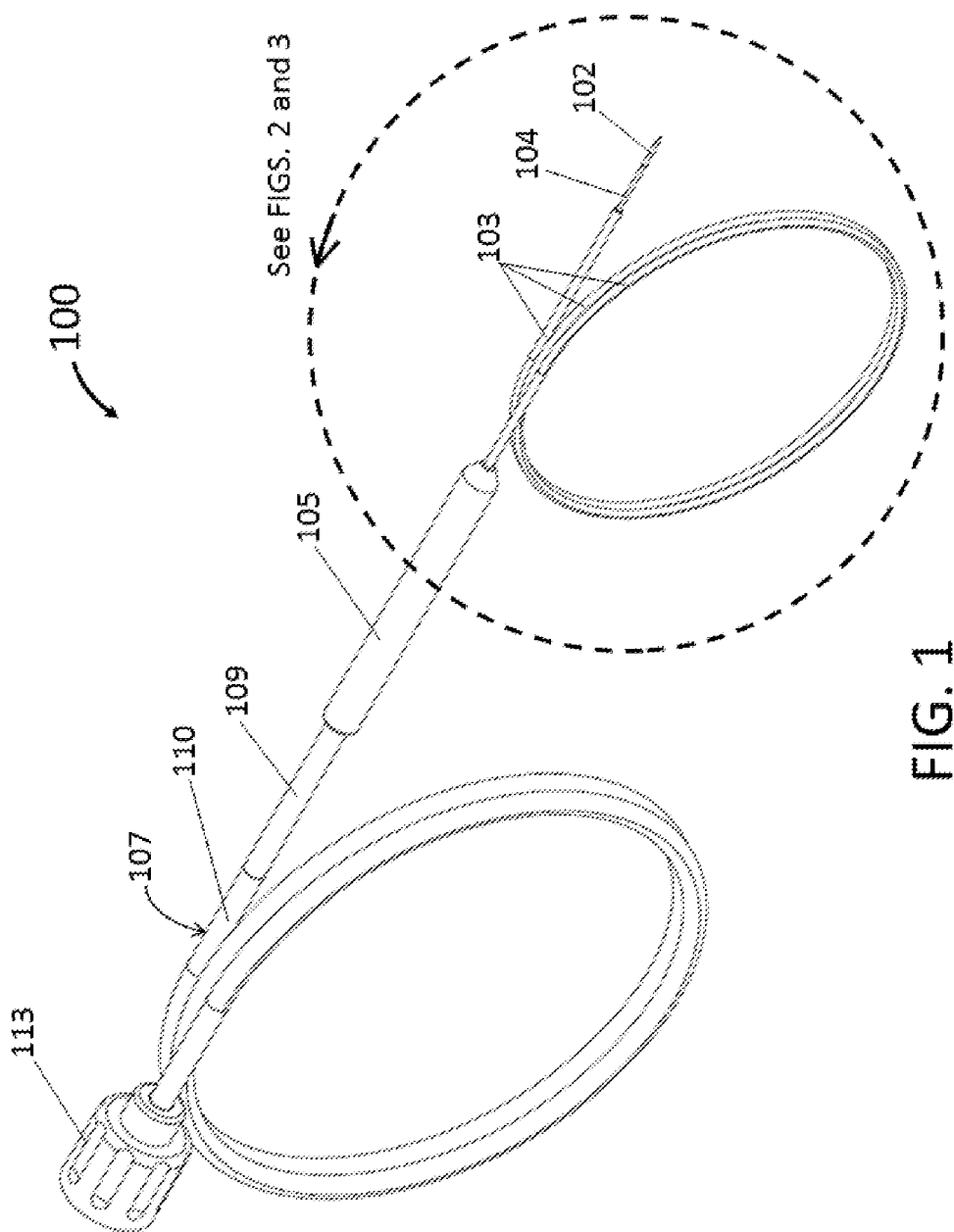
FIG. 1 is an external perspective view of an illustrative embodiment of the invention.

As illustrated in FIG. 1, the endoscopic cryoablation apparatus 100 comprises a cryoprobe tip 102 with an ablation zone 122 and integrated with a catheter shaft 104 such that a moveable sheath 103 covers and exposes the cryoprobe tip 102 by way of a controllable handle 105. As depicted, an umbilical 110 has an outer wall 107 and attaches to a connector 113 at a proximal end of the endoscopic cryoablation apparatus 100. The connector interconnects with a cryo-system, or cryogenic console (not depicted) to deliver cryogenic fluid to the cryoprobe tip 102. At a distal end, the cryoprobe tip 102 interconnects with a flexible catheter shaft 104. The flexible catheter shaft 104 has a polymeric composition with a diameter of between about 1 mm-5 mm, typically less than about 3.8 mm in diameter; and a length of between about ½ m-2 m, typically between about ½ m-1½ m. The catheter shaft 104 can be safely passed through an operative channel of a therapeutic echoendoscope as desired. The overall longitudinal length of the apparatus 100 is between about 3 m-6 m, or smaller in the range of between about 1 m-3 m. The diameter of the apparatus 100 varies along its longitudinal axis and may be between about 1 mm-10 mm, and even smaller in the range of about 1 mm-3 mm.

In one embodiment, the catheter shaft 104 extends through the handle 105 and attaches to the umbilical 110 via a transitional rigid portion 109, or retraction guide 109. The retraction guide 109 is a plastic portion that allows for attachment of the catheter 104 to the umbilical 110. The handle 105 is fixed to move in the x-y directional plane across the retraction guide 109 but may also be capable of rotational movement around the catheter shaft 104 and retraction guide 109. A protective outer sheath 103 covers a distal end of the catheter shaft 104 between the handle 105 and a needle probe tip 102. The sheath 103 is open-ended at the distal end to expose the needle probe tip 102 for penetration into a target tissue when the sheath 103 is retracted. The sheath 103 interconnects with the handle 105 for synchronous control, movement and retraction. The retraction guide 109 assists in translational movement of the handle 105 to move the sheath 103 translationally along the x-y directional axis of the catheter shaft 104. The sheath extends a length of between about 1 m to about 2 m between the handle 105 and the probe tip 102, as dependent on the length of the catheter shaft from the probe tip 102 to the handle 105. The handle is typically about 10 cm in length with a diameter between about 1 mm-5 mm and larger so that a catheter of that size and dimension can be positioned within.

FIGS. 2 and 3 illustrate the distal end of the endoscopic cryoablation catheter 100 such that cryogen supply line 106 and cryogen return line 108 are housed in the catheter shaft 104. The catheter shaft is insulated by heating elements 112. A lumen 126 between the return line and catheter shaft provides an insulative layer 126 to prevent freezing at an area external to the cryogen supply and return lines.

As shown in FIG. 2, the sheath 103 is protracted when the handle is moved or pushed toward the distal end of the apparatus 100 (as designated by the arrow 'x'). As shown in FIG. 3, retraction of the sheath exposes the probe tip 102 when the handle 105 is moved away from the distal end of the probe (as designated by the arrow 'y').

In addition, the catheter shaft 104 and umbilical 110 (see FIG. 1) are insulated throughout the lengths to prevent injury to nearby areas including anywhere along the endoscopic path, the region as defined by placement of the catheter shaft 104. For exemplary purposes, and not limitation, endoscopic paths may include passageways through the esophagus, stomach, endoscope or endoscopic lumen, visualization apparatus (e.g. EUS), or paths created by a physician's hand. As shown in FIGS. 2 and 3, the catheter shaft 104, outer sheath 103, and handle 105 include heating elements 112 (as indicated by the hash marks), or defrosting elements 112, that prevent the shaft from freezing to an endoscope. The heating elements 112 comprise one or more electrically conductive wires integrated within the catheter shaft, sheath, and handle but may also include a mesh of heating wire to promote a more uniform heat distribution. Any configuration of wires may be utilized including, but not limited to, linear configurations, spiral arrangements of wires, or mesh formations. The heating elements 112 apply mild heat adjacent structures to prevent freezing, such as to prevent freezing between the catheter shaft 104 and the sheath 103, as well as between the catheter shaft 104 and tissue along the endoscopic path. The heating elements 112 reduce, and preferably eliminate, risk of damage to non-target tissue areas as well as to an independently operated endoscope.

For exemplary purposes only, and not limitation, the endoscopic cryocatheter or the independently operated endoscope may integrate an optical visualization tool, an ultrasound device, magnetic resonance imaging (MRI), computed tomography (CT), or any other visualization technique, alone or in combination, and with any compatible tool or technique.

Referring to FIGS. 2 and 3, the endoscopic cryocatheter 100 is insulated along the length of the shaft 104. This insulation 126 is achieved by an insulative vacuum lumen 126 within the catheter shaft 104 upon which a vacuum is drawn. In FIG. 2, the probe tip 102 is covered by the sheath 103 (protracted configuration) when the handle is moved toward the distal end of the apparatus 100 (movement as indicated by the arrows). The probe tip and catheter are encased in the sheath 103 which covers the probe tip during catheter insertion to prevent damage to the endoscope, endoscopic cryocatheter 100, or puncture of tissue during endoscopic placement of the endoscopic cryocatheter 100 to an internal treatment site. In FIG. 3, the probe tip 102 is exposed when the handle 105 is moved towards the proximal end allowing the sheath 103 to retract at a tissue site designated for treatment. Additionally, any catheter or probe tip or configuration (needle, paddle, etc.) can be utilized and detachably affixed as long as it passes through the dimensions of the catheter sheath 104. When positioned to a treatment site through an endoscope (not illustrated), the sheath 103 is retracted to expose the ablation probe tip 102.

One embodiment of the probe tip 102 is illustrated as a needle-tip probe 102 capable of piercing a tissue. In one aspect, the needle-tip probe 102 is a sharp-pointed and stiff needle to penetrate the stomach wall and/or pancreatic parenchyma. The needle-tip probe 102 comprises an ablation zone, or freeze zone 122 at a far distal portion of the probe tip. The needle-tip probe 102 is about 1.5 mm in diameter by about 4 cm in length with an ablation zone of between about 10 mm-20 mm. Typically, the ablation zone is about 12 mm-15 mm in length, as dependent on the size of the needle tip probe. Any size, shape and dimension of needle can be utilized, as desired, depending on the tissue to be ablated. In addition, the probe tip 102 is compatible with a liquid or gas cryogen, or any cryogenic fluid, and allows the formation of ice at a tissue site. As such, the needle probe tip 102 is securely affixed to an internal wall of the catheter shaft 104 by a thermo-compatible adhesive. Thermal elements 146 in the probe tip 102 allow for thaw of the frozen tissue and release of the probe tip from the treated tissue (See depiction in FIGS. 2 and 3). The thermal elements 146 also act as spacers to maintain distance between the catheter shaft 104 and the supply and return lines. As illustrated here, the ablation zone 122 extends forward from the thermal elements 146 to the distal-most portion of the probe tip 102. Without limitation, the ablation zone may be created within any portion of the probe tip to integrate various portions, sizes, and dimensions as desired.

In another aspect, the sharp needle-like probe tip is capable of penetrating any desmoplasia, fibrous connective tissue, tumor infiltrate, and scar or fibrosis. Additionally, the sharpness of the needle-like probe tip can be used for EUS guided pseudocyst drainage during a procedure. The EUS cryoablation procedure provides surgeons with a minimally invasive tool that reduces morbidity and lowers costs.

In yet another aspect, the probe tip may be a blunt probe or catheter tip that forms an ablation zone at a focal point or along a linear path. Various embodiments of a probe tip may be incorporated herein without limitation.

One embodiment utilizes a catheter shaft 104 that interconnects with the probe tip 102 to provide continuous cryofluid delivery and return from the cryo-system. The connector 113 enables cryogen to run from the cryo-source at the proximal end of the apparatus 100 to the probe tip 102 at the distal end.

As depicted in FIGS. 4A and 4B, a distal end of an endoscopic cryoablation catheter 400 is magnified. A needle-tip probe 402 with an ablation zone 422 is connected to a catheter shaft 404 by way of an adhesive 444. Within the catheter shaft 404 is a supply line 406 defining a cryogen supply lumen 416 that runs longitudinally the length of the apparatus 400 and extends to a cryogen source at the console. The cryogen return line 408 circumferentially encases the supply line 406 such that a return lumen 418 is formed therebetween. Spacers 446 at the distal end of the needle-tip probe 402 maintain a space between the return line 408 and an inner surface 448 of the needle-tip probe. The supply line 406 and return line 408 run the length of the apparatus 400 (as similar to the invention as shown in FIG. 1). The coaxial design of cryogen supply line within the return line allows for more efficient use of space inside the catheter as compared to a side by side supply-return line design. Thus, the coaxial design provides catheter shafts having sizes as small as 0.5 mm or smaller; and catheter shafts can be manufactured up to about 1 cm or greater. In one aspect, the catheter shafts and probes can be interchanged depending on designated use in minimally invasive treatments and surgical, respectively. The catheter shaft 404 also creates an insulating lumen 423 to which an active or passive insulation can be applied. Active insulation is created when a vacuum is applied within the insulating lumen 423, or when heat is applied. Passive insulation allows gaseous components to occupy the insulating lumen 423, or where foam and other insulative materials are configured therein. See FIG. 4C which depicts a cut-away cross-section of FIG. 4A.

In the embodiment of the apparatus 400, as depicted in FIGS. 4A, 4B, and 4C, a thermal insulation 426 is utilized in both the catheter shaft 404 and the sheath 403. See hash marks within catheter shaft and sheath. The thermal insulation depicted includes an insulative thermoelectric mesh 426 that integrates a plurality of electrical wires. The wire mesh uniformly insulates the catheter and sheath from cryogenic temperatures. The heat applied to the catheter shaft 404 and to the sheath 403 prevents freezing of the catheter and sheath while protecting endoscopic walls and cryocatheter components, and shielding tissues that are not designated for treatment. In another aspect, the thermal insulation may include one or more thermo-electric resistance wires in a linear arrangement, spiral, or mesh configuration.

As depicted in FIGS. 4A, 4B, and 4C, several electrical and mechanical deflection wires 427 are integrated within an internal wall of the catheter shaft 404 and sheath 403 to move and steer the distal end at the probe tip 402. In one aspect, the sheath is the steerable portion that integrates deflection wires 427 and directs the probe tip to the tissue site. In another aspect, the catheter shaft integrates the deflection wires 427 that direct the distal end to the tissue site. Deflection wires may be integrated along any wall of the longitudinal length of the apparatus and controlled via the handle controls or at a main console.

Figure 5:
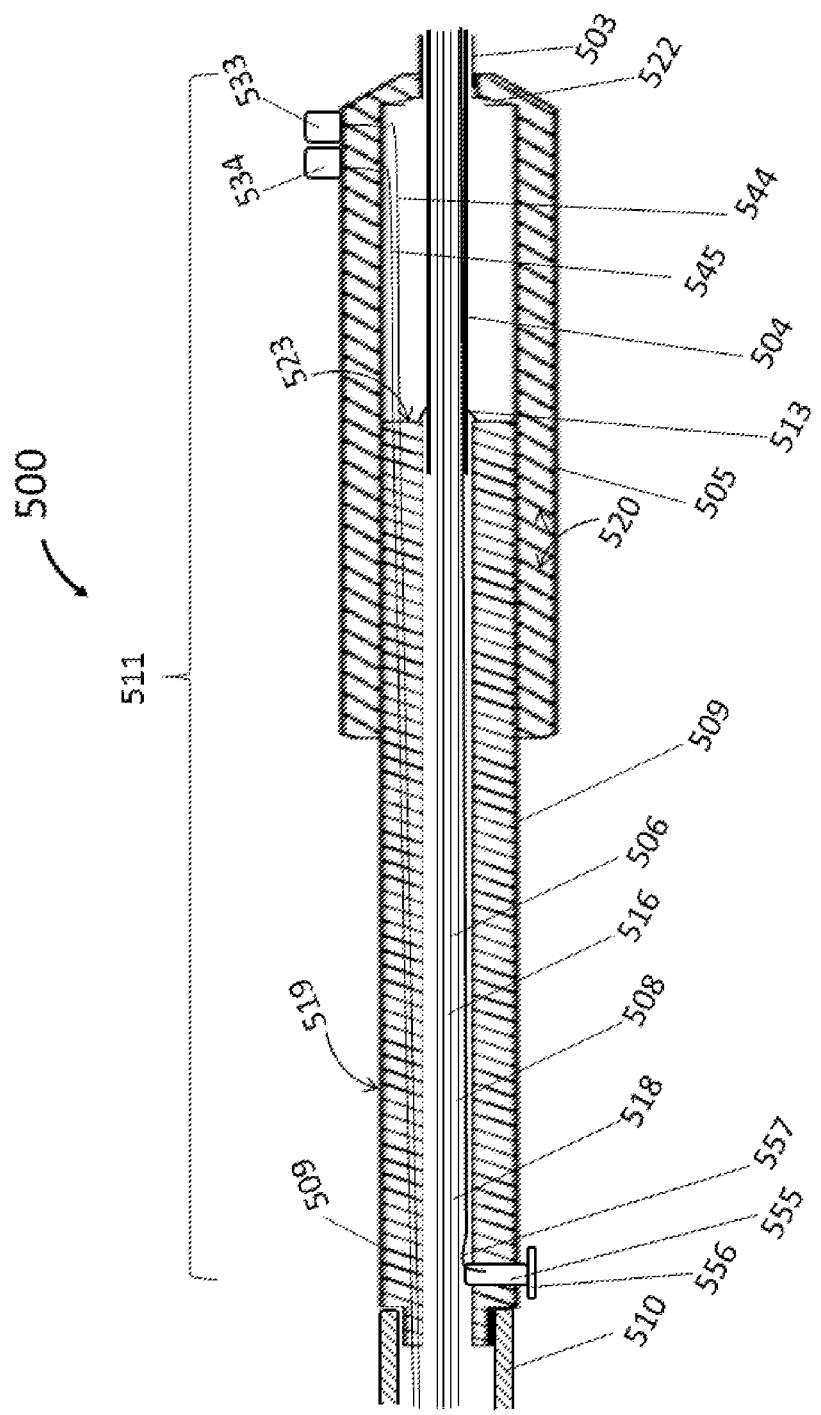
FIG. 5 is an embodiment of the invention with an internal view of the components in the handle portion.

In one aspect, an accessory injection tube 449 is positioned within the insulating lumen 423 and extends longitudinally along the catheter shaft 404. The accessory injection tube 449 emerges at the distal end of a needle tip 402 at an exit portal 447. (Another embodiment that utilizes an injection tube/channel that exits at the needle tip is illustrated in FIG. 5.) The accessory injection tube 449 allows for the introduction of drugs and therapeutic agents such as chemotherapeutic agents, gene therapy vectors and agents, hormones, vitamins, pro-apoptotic or anti-apoptotic agents, and clotting agents, for exemplary purposes and not limitation. The drugs and therapeutic agents can be introduced prior to, during and/or following an ablation procedure. Tissues and aspirate may also be withdrawn through the accessory tube 449.

An embodiment of the invention as shown in FIG. 5 illustrates a section of an endoscopic ablation catheter apparatus 500. Depicted is an umbilical 510 attached to a retraction guide 509. At an opposite end, a flexible catheter 504 is affixed to the retraction guide by adhesives 513 comprised of epoxy or cyanoacrylate adhesives, or other medical grade superglue. A handle 505 attaches to an outer sheath 503 at a distal end of the apparatus 500 such that the outer sheath 503 can be moved in the x-y directional axis as desired by the user. The handle 505 surrounds the catheter 504 and retraction guide 509 to form an integrated handheld portion 511. The handheld portion 511 also incorporates heating elements 520 to protect the user from cryo-temperatures generated within the device. As illustrated here, an internal forward stop 522 allows the handle 505 and sheath 503 to move back, synchronously, a pre-determined distance such that the handle covers a portion of the retraction guide 509. A reverse stop 523 of the retraction guide 509 allows the handle 505 and sheath 503 to be pushed forward a pre-determined distance over the catheter shaft 504. Distances can be indicated at 0.5 cm markings on the handle portion 511 to allocate the desired protraction and retraction of the sheath. Any desired increment, however, may be designated and marked. The markings allow the user to customize movement of the outer sheath 503 to a desirable location and keep record of the length of catheter shaft or probe tip exposed. Additionally, the sheath may be the limiting factor so as to designate the distance the handle is permitted to retract in which the sheath is not permitted to move beyond the larger diameter of the retraction guide.

As illustrated, a supply line 506 has an internal lumen 516 for delivery of cryogenic fluid to a probe tip. Return line 508 is positioned about the supply line to form a cylindrical lumen 518 disposed longitudinally with the supply line 506 throughout the length of the endoscopic cryoablation apparatus. Further, on/off controls 533 and 534 provide electrical connection 544 and 545, respectively, to allow the user to turn on/off the cryogen source, thaw, and/or heating elements 520. Other controls may be implemented to control gaseous discharge from the cryo-return lines, heating mechanisms throughout the length of the apparatus, temperatures adjustments, thermal monitoring, and visualization, among others. Automated operation of the apparatus may also be incorporated with the use of software based systems. In one aspect, automated control mechanisms also operate the sheath, individually or in combination with the handle. Further, the controls of the invention can be motorized for gradual precise positioning, as well as computerized to operate protraction and retraction of the sheath in synchrony with the handle. Any number of components of the invention may be motorized, computerized, and programmed as desired. Where the endoscopic cryocatheter is programmed, specific patient parameters may be integrated with a software program to facilitate placement of the probe tip, temperature adjustments, and treatment durations.

In another aspect, as shown in FIG. 5, the endoscopic cryoablation catheter 500 comprises an injection channel 555, access port 556, and accessory tube 557 for administering drugs, adjuvants, and therapeutic agents at the target tissue site. The access port 556 is a rigid twist lock 556 within the handheld portion 511, but may also be a flexible tube to allow introduction of an agent via a syringe or similar mechanism. The access port 556 is positioned on an outer wall 519 of the retraction guide 509 but may be positioned anywhere in the handle portion 511 or along the length of the umbilical 510 or catheter shaft 504. The injection channel 555 allows entry of the agent into the accessory tube 557; the accessory tube 557 then runs longitudinally the length of the catheter shaft 504 to the distal end at the probe tip. An exit portal (not depicted here) within the needle tip seals a terminal portion of the accessory tube 557 to the needle tip to prevent any cryogen leaking from the needle tip probe. The accessory tube 557 is configured adjacent to the return line 508, within or along the catheter shaft 504 to allow for the introduction of additional adjuvants and agents as used in therapies such as chemotherapy, gene therapy, hormone and vitamin therapies. Such agents may include chemotherapeutic agents, gene therapy vectors, hormones, vitamins, pro-apoptotic or anti-apoptotic agents, and clotting agents, among others. The agents may be introduced at any stage of the procedure, including before, during, or after an ablation procedure. This accessory channel 557, along with the injection channel 555 and access port 556 can also be utilized for the introduction of biopsy needle apparatus, aspiration of fluid or tissue, or other device as desired. Additionally, the introduction of other ablative devices such as RF, high frequency ultrasound (HiFU), laser, or other ablative energies can be introduced. These channels within or along the endoscopic cryocatheter allow for the application of multiple treatment modalities to more effectively destroy the target tissue.

Further, in another aspect, the flexible endoscopic catheter of the invention may integrate any ablative device within the internal lumen of the catheter so as to advantageously allow for a plurality of treatment modalities through an integral tube. The consolidation of ablation devices minimizes invasiveness in patient treatment as well as treatment times and duration of the overall procedure.

In one embodiment, the catheter assembly, including supply and return lines encompassed in a catheter shaft, is contained in a sheath which slides freely over the outer surface of the catheter shaft allowing for the covering and uncovering of the probe tip during insertion and retraction of the endoscopic cryocatheter. In another embodiment, a portion of the catheter assembly is positioned over the freely sliding sheath. The sheath may comprise an insulative heating element along a portion or entire length of the catheter shaft to prevent freezing between the cryocatheter assembly and a wall of an endoscope. Any portion of the catheter shaft or the entire shaft can include the heating elements or insulative materials. The sheath terminates at the handle of the cryocatheter assembly and is affixed to the handle wherein movement of the handle and sheath sub-assembly causes movement of the sheath forward and backward to cover or uncover the probe tip, respectively. The components may be individually attached and affixed via adhesive or injection molded to form an integral component, or integral handle and sheath sub-assembly. The cryogen supply and return lines continue through the handle and through the umbilical to the connector where the co-axial lines diverge into independent cryogen supply and return lines. The connector compatibly aligns and seals with a connection of a cryogen source console.

In addition, between the cryogen return line and the umbilical is a lumen in which a vacuum or other type of insulation can be applied. This provides additional insulation to prevent freezing between components of the apparatus. Within or along the umbilical, control lines and electrical wires to control thawing, thermal monitoring, sheath movement, catheter tip steering, and accessory channels may be contained. The lines may run in a secondary umbilical parallel to that of the cryogen lines if so desired. This would have the benefit of separating the electromechanical control lines from that of the cryolines. Beneficially, integration of the lines with a single umbilical has the advantage of reducing the overall size and footprint.

The device is designed to provide the physician with a tissue ablation zone by freezing the target cancer or unwanted tissue while reducing collateral damage to surrounding non-targeted areas. The cryoablation device allows for more effective, reproducible, and controllable tissue ablation to treat diseased tissue. Further, the materials designated for manufacturing the apparatus of the invention integrate stainless steel cryo-supply lines, polyamide return lines as configured for cryo-temperatures, and any combination thereof. The umbilical is composed of flexible materials as known in the art but may be modified to include plastics and polymeric combinations that are useful in the field of medicine.

One embodiment of the cryoablation catheter incorporates the use of an endoscopic ultrasound (EUS) device such that the endoscopic catheter apparatus 100 can be passed through an assessory channel of an existing EUS device. Once the endoscopic catheter is inserted and manipulated within proximity of a tissue site for treatment, the sheath is retracted to expose the needle cryoablation probe; and the probe is inserted into the target tissue under ultrasound or other means of visualization.

For exemplary purposes and not limitation, the endoscopic ablation catheter of the invention is utilized in ablating pancreatic tumor tissue. The catheter is inserted through an accessory port of the ultrasound endoscope through the stomach. Once positioned in the stomach nearest the adjacent pancreatic treatment area, the sheath is retracted and the probe inserted through the stomach wall into the pancreatic tumor, simultaneously. The steps of retracting the sheath and then inserting the probe may occur in two separate steps as selected during treatment. The cryoprobe is then activated to freeze the target tissue such that the distal-most portion of the needle-tip probe creates an ablation zone. The intermediary remainder of the needle that penetrates the stomach wall does not freeze and does not damage extraneous tissue outside the ablation zone. When freezing is completed, the tissue is allowed to thaw, either passively or actively via the integrated heating element within the probe. The thaw enables removal of the probe from the frozen tissue mass without an extensive time delay. In this regard, the integrated heating element within the tip of the cryoprobe can be activated to accelerate tissue thawing or probe release from the tissue (rapid release). In addition to thawing the tissue, elevated temperatures can be achieved with the heating elements to ablate selected tissue, thereby allowing for the dual application of cryoablation and hyperthermic (heat) ablation at a target tissue site.

In another aspect, the cryocatheter is inserted as described for a specified cryo-treatment while a chemotherapeutic agent, a gene therapy agent or vector, a cell therapy agent, radiation, a vitamin, an anti-apoptotic or pro-apoptotic agent, a clotting agent or other desired agent is administered to the target tissue region via one or more intergraded tubes/channels. The agents can be injected manually or automated with agent introduction points at the catheter handle or console. Addition of adjuvant or agent may occur prior to, during, or following the cryo-treatment procedure. Furthermore, collection of tissue biopsies or fluid/tissue aspiration can be accomplished through the introduction of a biopsy needle or application of an aspiration vacuum (vacuum, pump, suction, syringe or other means of aspiration) via one of the accessory channels.

As embodied in the invention, the device and procedure utilizes freezing in tandem with an endoscopic ultrasound device or any other type of endoscope. Additionally the device and procedure can be combined with any other ablation or anti-cancer therapy through the intergraded accessory tubes/channels within the cryocatheter assembly. The ECC device represents a significant advantage in the treatment of pancreatic and gastrointestinal cancers or other diseases.

Such benefits encompassed by the technology include the ability of the endoscopic compatible cryoablation probe/catheter to generate an ultracold cryo-lesion, enhancing destruction of cancer cells while minimizing side effects, and with the ability to rapidly ablate larger areas of pancreatic tissue. Furthermore, one embodiment of the invention utilizes a method for applying cryoablation via endoscopic access to the target tissue which can include the pancreas, intestine, or other portion of the gastrointestinal track.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth here-below not be construed as being order-specific unless such order specificity is expressly stated in the claim.

What is claimed is:

1. An endoscopic cryoablation apparatus having a longitudinal length with a proximal end and a distal end, and comprising:
   a catheter shaft housing a cryogen supply line and a cryogen return line, wherein said catheter shaft is flexible and composed of a polymeric composition;
   an insulative lumen circumferentially surrounding said cryogen return line and disposed within said catheter shaft;
   a stiff needle-tip probe affixed to an internal wall of said catheter shaft at said distal end and comprising an ablation zone, wherein said needle-tip probe is affixed to said catheter shaft via a thermo-compatible adhesive;
   a sheath positioned circumferentially about said catheter shaft and covering said stiff needle-tip probe when said endoscopic cryoablation apparatus is in a retracted position;
   a handle portion affixed to a proximal end of said sheath;
   an umbilical interconnected with said handle portion at a transitional portion, such that said supply line and said return line extend through said umbilical and along said longitudinal length;
   an accessory tube disposed within said insulative lumen and extending through said longitudinal length;
   an exit opening within said stiff needle-tip probe to administer at least one drug, adjuvant, or therapeutic agent to a tissue site, or to remove a tissue or a fluid from said tissue site via said accessory tube; and
   a connector positioned at said proximal end to interconnect said supply line and said return line with a cryogen console,
   wherein said sheath is moveable translationally relative to and along said catheter shaft, and
   wherein said endoscopic cryoablation apparatus is configured for use with an endoscope.

2. The endoscopic cryoablation apparatus of claim 1, wherein said handle and said sheath are integrated to allow movement of said sheath to expose said stiff needle-tip probe and cover said needle-tip probe.

3. The endoscopic cryoablation apparatus of claim 1, further comprising one or more thermal elements in said stiff needle-tip probe and disposed between said return line and said catheter shaft and within said insulative lumen.

4. The endoscopic cryoablation apparatus of claim 1, further comprising thermal insulation integrated in one or more of said catheter shaft, said handle, said umbilical, said transitional portion, and said sheath.

5. The endoscopic cryoablation apparatus of claim 4, wherein said thermal insulation comprises thermoelectric resistance wire in a linear configuration, spiral arrangement, or mesh formation.

6. The endoscopic cryoablation apparatus of claim 1, wherein said handle comprises controls to operate one or more of cryogen delivery, temperature, and said thermal insulation.

7. The endoscopic cryoablation apparatus of claim 1, wherein said handle is a rigid retraction guide that provides a forward stop and a reverse stop in moving said sheath.

8. The endoscopic cryoablation apparatus of claim 1, wherein said sheath is moveable rotationally about said catheter shaft.

9. The endoscopic cryoablation apparatus of claim 1, further comprising one or more mechanical deflection wires positioned within said longitudinal length to direct said catheter shaft and said stiff needle-tip probe to and from a tissue site.

10. The endoscopic cryoablation apparatus of claim 9, wherein at least one of said one or more mechanical deflection wires is positioned within said sheath, said catheter shaft, or both.

11. The endoscopic cryoablation apparatus of claim 1, further comprising one or more wires positioned within said longitudinal length to provide power to at least one of: said catheter shaft, said sheath, and said stiff needle-tip probe.

12. The endoscopic cryoablation apparatus of claim 11, wherein said one or more wires comprise one or more electrically conductive wires in a linear configuration, spiral arrangement, or mesh formation.

13. The endoscopic cryoablation apparatus of claim 1, further comprising one or more heating elements within said needle-tip probe for thermal ablation or hyperthermic ablation at a target tissue site.

14. The endoscopic cryoablation apparatus of claim 13, further comprising one or more wires positioned within said longitudinal length to provide power to said one or more heating elements.

15. The endoscopic cryoablation apparatus of claim 1, wherein said catheter shaft has a length of about 0.5 meters to about 2.0 meters.

16. The endoscopic cryoablation apparatus of claim 1, wherein said catheter shaft has a diameter of about 1.0 millimeters to about 4.0 millimeters.

17. The endoscopic cryoablation apparatus of claim 1, wherein said sheath is composed of a polymeric composition.

18. The endoscopic cryoablation apparatus of claim 1, wherein said stiff needle-tip probe is at least partially exposed by said sheath while said sheath is positioned within an operative channel of said endoscope.

19. An apparatus for endoscopic ablation therapy comprising:
   a cryogen supply line and a cryogen return line surrounded by a catheter shaft, such that said cryogen supply line, said cryogen return line, and said catheter shaft run longitudinally from a proximal end to a distal end at an ablation zone; wherein said distal end of said catheter shaft is covered by a sheath that interconnects with a handle, and said sheath is moveable translationally relative to and along an exterior of said catheter shaft,
   an insulative lumen circumferentially surrounding said cryogen return line and disposed within said catheter shaft,
   a stiff needle-tip probe affixed to an internal wall of said catheter shaft at a distal end of said catheter shaft, wherein said needle-tip probe is affixed to said catheter shaft via a thermo-compatible adhesive,
   an accessory tube disposed within said insulative lumen and extending longitudinally from said proximal end to said distal end; and
   an exit opening within said stiff needle-tip probe to administer at least one drug, adjuvant, or therapeutic agent to a tissue site, or to remove a tissue or a fluid from said tissue site via said accessory tube, wherein at least a portion of said catheter shaft is within an operative channel of an endoscope.

20. The apparatus of claim 19, wherein said stiff needle-tip probe is positioned at said distal end and connected to said cryogen supply line, said cryogen return line, and said catheter shaft, and wherein said stiff needle-tip probe comprises said ablation zone.

21. The apparatus of claim 19, wherein said handle retracts and protracts said sheath.

22. The apparatus of claim 19, further comprising one or more heating elements for thermal ablation or for thawing at said distal end, wherein said one or more heating elements are disposed between said return line and said catheter shaft and within said insulative lumen.

23. The apparatus of claim 19, wherein said catheter shaft and said sheath are flexible.

24. The apparatus of claim 23, wherein said catheter shaft and said sheath are composed of a polymeric composition.

25. The apparatus of claim 19, further comprising one or more wires positioned within said longitudinal length to provide power to at least one of: said catheter shaft, said sheath, and a needle-tip probe.

26. The apparatus of claim 25, wherein said one or more wires comprise one or more electrically conductive wires in a linear configuration, spiral arrangement, or mesh formation.

27. The apparatus of claim 19, further comprising one or more heating elements within a stiff needle-tip probe for thermal ablation or hyperthermic ablation at a target tissue site.

28. The apparatus of claim 27, further comprising one or more wires positioned within said longitudinal length to provide power to said one or more heating elements.

29. The apparatus of claim 19, wherein said stiff needle-tip probe is at least partially exposed by said sheath while said sheath is positioned within said operative channel of said endoscope.

* * * * *